United States Patent [19]

Onopchenko et al.

[11] Patent Number: 5,208,390
[45] Date of Patent: May 4, 1993

[54] PROCESS FOR ALKYLATING AROMATIC POLYOLS WITH HIGHER CARBON NUMBER ALPHA OLEFIN OLIGOMERS

[75] Inventors: Anatoli Onopchenko, Concord; Brian R. Kennedy, San Rafael, both of Calif.

[73] Assignee: Chevron Research and Technology Company, San Francisco, Calif.

[21] Appl. No.: 782,935

[22] Filed: Oct. 25, 1991

[51] Int. Cl.$^5$ ...................... C07C 37/14; C07C 39/12
[52] U.S. Cl. .................................. 568/766; 568/720; 568/788; 568/793
[58] Field of Search ................ 568/720, 766, 788, 793

[56] References Cited

U.S. PATENT DOCUMENTS

| | | | |
|---|---|---|---|
| 3,382,283 | 12/1966 | Zundel | 568/766 |
| 4,209,648 | 6/1980 | Cottman | 568/766 |
| 4,632,771 | 12/1986 | Liston et al. | 568/766 |

*Primary Examiner*—Werren B. Lone
*Attorney, Agent, or Firm*—Richard C. Gaffney

[57] ABSTRACT

A process for alkylating an aromatic polyol, such as catechol, with an alpha olefin oligomer of alpha olefins having from about 8 to 14 carbon atoms or mixtures thereof using an organic sulfonic acid catalyst which is soluble under the alkylation reaction conditions. The liquid alkyl aromatic polyol product is useful as a lubricating oil additive or lubricating oil base stock.

22 Claims, No Drawings

PROCESS FOR ALKYLATING AROMATIC POLYOLS WITH HIGHER CARBON NUMBER ALPHA OLEFIN OLIGOMERS

FIELD OF THE INVENTION

This invention relates to an improved process for alkylating aromatic polyols, such as catechol, with oligomers derived from alpha olefins having from 8 to 14 carbon atoms. The alkylated products are useful in the manufacture of lubricating oil base stocks and lubricating oil additives. More particularly, this invention relates to the alkylation of aromatic polyols with alpha olefin oligomers using a sulfonic acid catalyst which is soluble under the alkylation reaction conditions.

BACKGROUND OF THE INVENTION

Alkyl aromatic polyols, such as alkyl catechols, are useful as antioxidant and friction-modifying additives for lubricating oils. Borated alkyl catechols also find use as lubricating oil additives to reduce engine wear and deposits, thus increasing the useful life of automobile and truck engines.

These alkyl aromatic polyols are typically prepared by alkylating an aromatic polyol with an olefin. Typical olefins used to alkylate aromatic polyols include readily available $C_{14}$ to $C_{28}$ alpha olefins, polypropylenes and polybutenes. The alkyl group is generally of sufficient carbon number to allow the alkyl aromatic polyol to be soluble in lubricating oil.

The alkylation of aromatic polyols with olefins generally requires a catalyst, such as a Lewis acid or a Brönsted acid. Sulfonic acid resins and polymers, such as Amberlyst-15 ®, Amberlyst-36 ® and Nafion-H ®, are frequently used as the catalyst for such reactions, since these materials are insoluble under the reaction conditions and are easily recovered from the reaction mixture by simple filtration.

For example, U.S. Pat. No. 4,632,771, issued Dec. 30, 1986 to T. V. Liston et al., describes the alkylation of catechol with $C_{14}$ to $C_{18}$ alpha olefins, containing less than 20% $C_{18}$ content, using the sulfonic acid resin, Amberlyst-15 ®, as a catalyst. Similarly, U.S. Pat. No. 4,643,838, issued Feb. 17, 1987 to T. V. Liston et al., describes the alkylation of catechol with $C_{18}$ to $C_{24}$ olefin mixtures, containing at least 30% branched olefins, using Amberlyst-15 ® as a catalyst. The alkyl catechol products of these patents are described as being normally liquid at typical storage temperatures.

Similarly, phenol has been alkylated with alpha olefin oligomers using Amberlyst-15 ®. PCT International Publication No. WO 90/07564, published Jul. 12, 1990, discloses liquid alkylphenyl poly(oxypropylene) aminocarbamate fuel and lubricating oil additives and describes the alkylation of phenol with alpha olefin oligomers derived from $C_8$ to $C_{20}$ alpha olefins using Amberlyst-15 ® as a catalyst.

Thus, using these previously described procedures, the alkylation of aromatic polyols, such as catechol, with high carbon number alpha olefin oligomers was expected to provide compounds useful for many lubricating oil applications. The unique structure of higher carbon number alpha olefin oligomers was expected to give an aromatic polyol alkylated with such olefins excellent solubility and compatibility in lubricating oils, especially in synthetic or semi-synthetic lubricating oils which consist, at least in part, of hydrogenated alpha olefin oligomers.

Unfortunately, all attempts to alkylate catechol with alpha olefin oligomers derived from $C_8$ to $C_{14}$ alpha olefins using insoluble sulfonic acid catalysts proved unsuccessful. Little or no alkylated products were produced under the normal alkylation reaction conditions even with prolonged reaction times. Thus, a need exists for a new process for alkylating aromatic polyols with high carbon number alpha olefin oligomers.

It has now been found that aromatic polyols can be alkylated with alpha olefin oligomers of alpha olefins having about 8 to 14 carbon atoms using an organic sulfonic acid catalyst, which is soluble under the alkylation reaction conditions, to produce a liquid alkyl aromatic polyol.

Soluble sulfonic acid catalysts have been used previously to alkylate phenol. For example, U.S. Pat. No. 2,865,966, issued Dec. 23, 1958 to B. Y. Abadir, teaches the alkylation of phenol with an acyclic polypropylene in the presence of a hydrate of toluene sulfonic acid.

U.S. Pat. No. 3,932,537, issued Jan. 13, 1976 to W. H. Wetzel et al., teaches the use of either an aryl sulfonic acid having a K value of at least $3.8 \times 10^{-3}$ or trifluoromethanesulfonic acid as the catalyst for alkylating a phenol with an alkylating agent consisting of aliphatic olefins having from 2 to about 20 carbon atoms.

U.S. Pat. No. 4,418,222, issued Nov. 29, 1983 to L. R. Honnen, teaches a continuous process for producing para alkyl phenols by reacting phenol with polypropylene in the presence of trifluoromethanesulfonic acid.

These patents, however, do not teach the alkylation of an aromatic polyol, such as catechol, with higher carbon number alpha olefin oligomers.

SUMMARY OF THE INVENTION

It has now been discovered that aromatic polyols can be alkylated with higher carbon number alpha olefins using a sulfonic acid catalyst which is soluble under the alkylation reaction conditions. The resulting alkyl aromatic polyols are liquids at ambient temperatures.

The present invention provides a process for the alkylation of an aromatic polyol, having from 1 to 3 aromatic rings and from 2 to 4 hydroxy groups with at least two of the hydroxy groups directly connected to adjacent aromatic ring carbon atoms, with an alpha olefin oligomer of an alpha olefin having from 8 to 14 carbon atoms. The alkylation reaction is conducted in the contact presence of a catalytic amount of an organic sulfonic acid catalyst which is soluble under the alkylation reaction conditions. After the alkylation reaction, a liquid alkyl aromatic polyol product is recovered.

DETAILED DESCRIPTION OF THE INVENTION

The present invention relates to an improved process for alkylating aromatic polyols with alpha olefin oligomers using a sulfonic acid catalyst which is soluble under the alkylation reaction conditions. The aromatic polyols have from 1 to 3 aromatic rings and from 2 to 4 hydroxyl groups wherein at least two of the hydroxyl groups are in vicinal (adjacent) positions on the aromatic ring carbon atoms.

Preferably, the aromatic polyol is an aromatic compound having the formula:

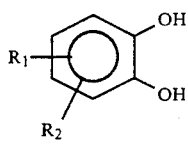

wherein $R_1$ and $R_2$ can be the same or different and are selected from the group consisting of hydrogen, hydroxy, lower alkyl of 1 to 8 carbon atoms, and lower alkoxy of 1 to 8 carbon atoms. More preferably, $R_1$ is hydrogen, hydroxy, lower alkyl, or lower alkoxy; and $R_2$ is hydrogen or hydroxy. Still more preferably, $R_1$ is hydrogen, hydroxy, or lower alkyl and $R_2$ is hydrogen. Most preferably, $R_1$ and $R_2$ are hydrogen.

The term "lower alkyl" refers to both straight- and branched-chain groups having a total of from 1 to 8 carbon atoms and includes primary, secondary and tertiary alkyl groups. Typical lower alkyls include, for example, methyl, ethyl, n-propyl, isopropyl, t-butyl, t-octyl and the like.

The term "lower alkoxy" refers to the group $OR_3$ where $R_3$ is lower alkyl. Typical lower alkoxy groups include, for example, methoxy, ethoxy and the like.

Aromatic polyols suitable for use include, but are not limited to:
1,2-benzenediol (catechol);
3-methyl-1,2-benzenediol;
4-methyl-1,2-benzenediol;
3-ethyl-1,2-benzenediol;
4-ethyl-1,2-benzenediol;
3-tert-butyl-1,2-benzenediol;
4-tert-butyl-1,2-benzenediol;
3-tert-octyl-1,2-benzenediol;
4-tert-octyl-1,2-benzenediol;
3-methoxy-1,2-benzenediol;
4-methoxy-1,2-benzenediol;
3-ethoxy-1,2-benzenediol;
4-ethoxy-1,2-benzenediol;
1,2,3-benzenetriol (pyrogallol);
1,2,4-benzenetriol (hydroquinol);
1,2,3,5-benzenetetrol;
1,2,4,5-benzenetetrol;
1,2,3,4-benzenetetrol (apionol);
1,2-naphthalenediol;
2,3-naphthalenediol;
1,2,3-naphthalenetriol;
1,2,4-naphthalenetriol;
1,2,5-naphthalenetriol;
1,2,6-naphthalenetriol;
1,2,7-naphthalenetriol;
2,3,6-naphthalenetriol;
1,2,4,5-naphthalenetetrol; and
1,2,4,7-naphthalenetetrol.
Preferred aromatic polyols are catechol and pyrogallol, most preferred is catechol.

In the process of the present invention, an aromatic polyol is alkylated with an alpha olefin oligomer or mixture of oligomers. Suitable alpha olefin oligomers are prepared or derived from alpha olefins having about 8 to 14 carbon atoms.

The term "alpha olefin" as used herein refers generally to 1-olefins, wherein the double bond is at the terminal position of an alkyl chain. Alpha olefins having about 8 to 14 carbon atoms are generally 1-olefins, but may contain minor amounts of olefins having the double bond isomerized to an internal or vinylidene position.

The term "alpha olefin oligomer(s)" as used herein means the unhydrogenated trimers, tetramers and pentamers and mixtures thereof prepared or derived from alpha olefins having about 8 to 14 carbon atoms. Such alpha olefin oligomers may include minor amounts of dimers of alpha olefins having about 8 to 14 carbon atoms, but such dimers are not preferred. Preferably, the alpha olefin oligomers are prepared from alpha olefins having 10 to 12 carbon atoms. Most preferred are alpha olefin oligomers of 1-decene.

The alpha olefin oligomers used herein are prepared by methods well-known in the art. For example, these oligomers can be prepared using boron trifluoride catalysts as described in U.S. Pat. Nos. 4,238,343 and 4,045,507, and in Onopchenko, et al., *BF3-Catalyzed Oligomerization of Alkenes* (Structure, Mechanisms and Properties), 183rd ACS Natl. Meet. (Las Vegas, March 1982), *Ind. Eng. Chem., Prod. Res. Dev.*, 22(2), 182-91 (June 1983).

Preferred alpha olefin oligomers contain 24 to 60 carbon atoms, preferably 30 to 50 carbon atoms. Preferred alpha olefin oligomers include, for example, $C_8$ trimers, tetramers and pentamers; $C_{10}$ trimers, tetramers and pentamers; $C_{12}$ trimers and tetramers; and $C_{14}$ trimers and tetramers and mixtures thereof.

The structure of alpha olefin oligomers is complex due to numerous isomerizations and skeletal rearrangements which can occur during the course of the oligomerization reaction. A suggested mechanism for these isomerizations and rearrangements is described in Shubkin et al., *Ind. Eng. Chem. Prod. Res. Dev.*, 1980, 19, 15-19.

Generally, alpha olefin oligomers have a structure consisting of primarily disubstituted and trisubstituted olefins. The disubstituted olefins are either branched or linear and the trisubstituted olefins are branched as shown in Formulas I, II, and III:

Linear Internal Disubstituted Olefin (I)

Branched Terminal Disubstituted Olefin (II)

Branched Trisubstituted Olefin (III)

where $R^i$, $R^{ii}$ and $R^{iii}$ are the same or different and represent the remaining carbon atoms of the oligomerized alpha olefins. The alkyl groups attached to the olefin bond, i.e. $R^i$, $R^{ii}$ and $R^{iii}$, generally contain at least $n-2$ carbon atoms, where n is the carbon number of the starting alpha olefin.

For example, an alpha olefin trimer includes, among other structural isomers, a branched internal trisubstituted olefin which can be represented by the formula:

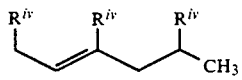

wherein $R^{iv} = n-2$, and n is the carbon number of the starting alpha olefin.

Generally, the alpha olefin oligomers which find use in the process of the present invention contain greater than 85 percent branched olefins, preferably greater than 90 percent branched olefins. The term "branched olefin(s)" as used herein refers to olefins having dialkyl substitution at the same carbon of the olefin bond and includes olefins having a branched terminal disubstituted structure (Formula II) and a branched trisubstitued structure (Formula III). The structure of alpha olefin oligomers, i.e. whether the olefin is linear or branched, can be determined using nuclear magnetic resonance (NMR) spectroscopy techniques which are well-known in the art. See, for example, U.S. Pat. No. 4,914,246, which is incorporated herein by reference.

As discussed hereinabove, the acidic catalysts commonly employed to catalyze the alkylation of phenolic compounds with olefins are not useful for the alkylation of aromatic polyols with alpha olefin oligomers.

It has been discovered however, that aromatic polyols can be alkylated with alpha olefin oligomers using an organic sulfonic acid catalyst which is soluble under alkylation reaction conditions. By the term "soluble under alkylation reaction conditions", it is meant that a catalytic amount of the sulfonic acid catalyst is soluble in the reaction mixture containing the aromatic polyol reactant and the alpha olefin oligomer reactant under the alkylation reaction conditions. Preferably, the reaction mixture comprising an aromatic polyol, an alpha olefin oligomer and the sulfonic acid catalyst is essentially homogeneous.

The catalyst should also be soluble in polar solvents such as water or alcohols or mixtures thereof to allow the catalyst to be extracted from the reaction mixture after the alkylation reaction is complete.

Suitable sulfonic acid catalysts include, for example, benzenesulfonic acid; 2,5-dimethylbenzenesulfonic acid; methanesulfonic acid; α- and β-naphthalenesulfonic acid; ortho-, meta- and para-toluenesulfonic acid, and trifluoromethanesulfonic acid. Such sulfonic acid catalysts are commercially available from a number of sources, such as Aldrich Chemical Company, Inc., Milwaukee, Wis. 53233.

Preferably, the catalyst is an aromatic sulfonic acid which is capable of undergoing a desulfonation reaction and is thus easily removed from the reaction mixture. Desulfonation of aromatic sulfonic acid catalysts is typically achieved by heating the reaction mixture to about 135° to 200° C. in the presence of water, steam, or dilute aqueous sulfuric acid. Desulfonation is further described, for example, in H. Cerfonain, *Mechanistic Aspects in Aromatic Sulfonation and Desulfonation*, Interscience Publishers, New York, N.Y., pp. 188-201. Especially preferred aromatic sulfonic acid catalysts are para-toluenesulfonic acid and benzenesulfonic acid.

The sulfonic acid catalyst will generally be present in the alkylation reaction mixture in an amount ranging from about 0.05 to about 10 weight percent, preferably 0.1 to 5 weight percent, based on the total weight of the reactants, i.e. the aromatic polyol and the alpha olefin oligomer. The ratio of aromatic polyol to alpha olefin oligomer will generally range from about 10:1 to 0.5:1, preferably from 5:1 to 1:1, and most preferably about 1:1.

The alkylation reaction will generally be conducted at a temperature ranging from about 50° C. to about 200° C., preferably from 90° C. to 185° C., and most preferably from 100° C. to 150° C. A reaction pressure will generally be maintained which is sufficient to keep the reactants in the liquid phase. Such pressures generally range from about 1 to 15 atmospheres. The alkylation reaction is preferably conducted at atmospheric or ambient pressure.

The alkylation reaction time will vary depending on the reaction temperature, pressure, concentration, mole ratio of reactants, and other factors. Generally, reaction times will be from 15 minutes to 48 hours, preferably from 30 minutes to 24 hours, and most preferably from 1 to 12 hours.

The alkylation reaction can be conducted in the absence of solvent or in the presence of an inert solvent. The use of solvents, particularly in batch reactor, greatly facilitates the process due to improved mixing of the reactants. Examples of inert solvents include benzene, toluene, xylene, chlorobenzene, and Chevron 250, 265 or 350 thinners, which are mixtures of aromatics, paraffins, and naphthenes. Other inert solvents may also be used.

The alkyl aromatic polyols produced by the process of this invention are mixtures of monoalkyl and dialkyl aromatic polyol structures. As used herein, the term "alkyl aromatic polyol(s)" refers to an aromatic polyol which has been alkylated on an aromatic ring carbon atom with an alpha olefin oligomer. Preferably, the alpha olefin oligomer-derived alkyl group is attached at an aromatic ring carbon atom which is in an ortho or para position relative to a hydroxy group of the aromatic polyol.

The alkyl aromatic polyol products of this process are liquid at room temperature. The term "liquid" as used herein in reference to the alkyl aromatic polyol product means there is no solidification or haziness in the product at ambient or room temperature (about 25° C.). It is important that lubricating oil additives do not form solids or waxes during storage, handling or actual use. Such solids can plug in-line filtering devices normally found in additive distribution systems and in actual engines. Such plugging can be catastrophic and must be avoided. Liquid additives, such as those produced by the process of the present invention, avoid such problems.

When the aromatic polyol is catechol, the product monoalkyl catechol has the preferred formula:

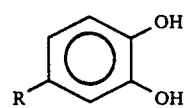

wherein R is an alpha olefin oligomer-derived alkyl group containing 24 to 60 carbon atoms, preferably 30 to 50 carbon atoms, or mixtures thereof.

The product monoalkyl catechol may also contain a monoalkyl catechol having the formula:

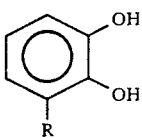

wherein R is as defined hereinabove.

Dialkyl catechol products have the formulae:

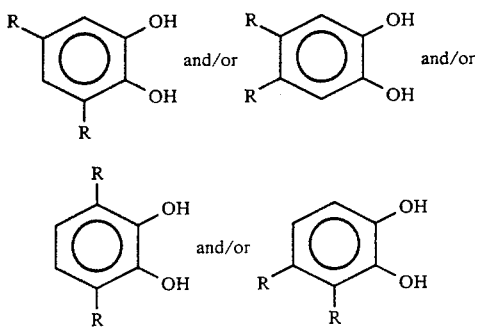

wherein R is as defined hereinabove.

The advantages of the present invention will be readily apparent from consideration of the following examples. These examples are provided for the purposes of illustration and comparison only and should not be interpreted as limiting the scope of the present invention.

EXAMPLES

Example 1 (Comparative)

Alkylation of Catechol with Oligomers of 1-Decene Using Amberlyst-15 ®

A mixture of catechol (49.2 g, 0.45 mol), unhydrogenated oligomers of 1-decene (202.4 g, 0.4 mol; $C_{30}$, 62%; $C_{40}$, 28%; $C_{50}$, 10%; average, $C_{35}$; containing 90% branched olefins) and Amberlyst-15 ® (20 g) was heated with stirring in chlorobenzene (300 mL) at 135° C. for 10 hours. Amberlyst-15 ® is a strongly acidic sulfonic acid ion-exchange resin available from Rohm and Haas, Philadelphia, Pa. A sample of the heterogeneous mixture was filtered hot, dissolved in n-hexane (200 mL), and washed four times with aqueous isopropanol (100 mL, water/alcohol, 75/25, v/v). The solvent was then removed on a rotary evaporator under reduced pressure (0.5 mm Hg) to give 200 grams of an oily material. Analysis by supercritical fluid chromatography (SFC) showed the oily material to consist essentially of the starting alpha olefin oligomers. Therefore, no significant alkylation of catechol occurred using Amberlyst-15 ® as a catalyst.

Example 2 (Comparative)

Alkylation of Catechol with Oligomers of 1-Decene Using Amberlyst-36 ®

A mixture of catechol (21.9 g, 0.2 mol), unhydrogenated oligomers of 1-decene (100 g, 0.2 mol; $C_{30}$, 62%; $C_{40}$, 28%; $C_{50}$, 10%; average $C_{35}$; containing 90% branched olefins) and Amberlyst-36 ® was heated with stirring at 140° C. for 20 hours. Amberlyst-36 ® is a polystyrene sulfonic acid resin available from Rohm and Haas, Philadelphia, Pa. The heterogeneous reaction mixture was filtered hot, dissolved in 200 mL n-hexane, and washed four times with 100 mL portions of aqueous isopropanol (water/alcohol, 75/25, v/v). The solvent was removed in a rotary evaporator by heating to 70° C. at 0.5 mm Hg to give 98 grams of lightly colored oily material. Analysis by SFC showed the oily material to consist essentially of the starting alpha olefin oligomers. Therefore, no significant alkylation of catechol occurred using Amberlyst-36 ® as a catalyst.

Example 3 (Comparative)

Alkylation of Catechol with Oligomers of 1-Decene Using XU-40036 Catalyst

A mixture of catechol (21.9 g, 0.2 mol), unhydrogenated oligomers of 1-decene (100 g, 0.2 mol, $C_{30}$, 62%; $C_{40}$, 28%; $C_{50}$, 10%; average $C_{35}$; containing 90% branched olefins), and XU-40036 catalyst (7 g) was heated with stirring at 140° C. for 20 hours. XU-40036 is an alumina supported fluorocarbon sulfonic acid polymer available from Dow Chemical Company. The heterogeneous reaction mixture was filtered, dissolved in 200 mL of n-hexane, and washed four times with 100 mL portions of aqueous isopropanol (water/alcohol, 75/25, v/v). The solvent was removed on a rotary evaporator under reduced pressure (0.5 mm Hg) to give 93 grams of oily material. Analysis by SFC showed the oily material to consist essentially of the starting alpha olefin oligomers. Therefore, no significant alkylation of catechol occurred using XU-40036 catalyst.

Example 4 (Comparative)

Alkylation of Catechol with Oligomers of 1-Decene Using Nafion-H ®

A mixture of catechol (6.8 g, 0.06 mol), unhydrogenated oligomers of 1-decene (28.3 g, 0.06 mol, $C_{30}$, 62%; $C_{40}$, 28%; $C_{50}$, 10%; average $C_{35}$; containing 90% branched olefins), and Nafion-H ® catalyst (0.3 g) was heated with stirring at 140° C. for 20 hours. Nafion-H ® is a perfluorinated sulfonic acid resin catalyst available from Du Pont. The heterogeneous reaction mixture was filtered, dissolved in n-hexane, and washed four times with aqueous isopropanol (water/alcohol, 75/25, v/v). The solvent was removed on a rotary evaporator under reduced pressure (0.5 mm Hg) to give 25 grams of an oily material. Analysis by SFC showed the oily material to consist essentially of the starting alpha olefin oligomers. Therefore, no significant alkylation of catechol occurred using Nafion-H ® catalyst.

Example 5

Alkylation of Catechol with Oligomers of 1-Decene Using Methanesulfonic Acid

A mixture of catechol (21.9 g, 0.2 mol), unhydrogenated oligomers of 1-decene (100 g, 0.2 mol, $C_{30}$, 62%; $C_{40}$, 28%; $C_{50}$ 10%; average $C_{35}$; containing 90% branched olefins) and methanesulfonic acid (2.2 g) was heated with stirring at 140° C. for 7 hours. The homogeneous mixture was cooled to room temperature, dissolved in n-hexane (200 mL), and washed five times with 100 mL portions of aqueous isopropanol (water/alcohol, 75/25, v/v). The solvent was removed by heating to about 120° C. under reduced pressure (0.5 mm Hg) to give 111 grams of a dark amber liquid product. The product had a hydroxyl number of 130 mg KOH/g, compared to the expected 188 mg KOH/g, or about 69% conversion. Analysis by SFC showed a conversion of about 64%.

Example 6

Alkylation of Catechol with Oligomers of 1-Decene Using p-Toluenesulfonic Acid

The procedure of Example 5 was repeated using p-toluenesulfonic acid (3 g) as the catalyst instead of methanesulfonic acid. After work-up as in Example 5, 108 grams of a dark amber liquid product was isolated. This product had a hydroxyl number of 116 mg KOH/g, corresponding to a conversion of about 61%. Analysis by SFC showed a conversion of about 55%.

Example 7

Alkylation of Catechol with Oligomers of 1-Decene Using Trifluoromethanesulfonic Acid

A mixture of catechol (493 g, 4.48 mol), unhydrogenated oligomers of 1-decene (2024 g, 4.03 mol; $C_{30}$, 62%; $C_{40}$, 28%; $C_{50}$, 10%; average $C_{35}$; containing 90% branched olefins), and trifluoromethanesulfonic acid (49 g) was heated with stirring at 135° C. for 4 hours. The homogeneous reaction mixture was cooled to room temperature, dissolved in n-hexane (500 mL), and washed five times with 1 L portions of aqueous isopropanol (water/alcohol, 75/25, v/v). The solvent was removed in a rotary evaporator by heating to about 70° C. at 0.5 mm Hg to give 2330 grams of a dark amber liquid product. The product had a hydroxyl number of 152 mg KOH/g, corresponding to a conversion of about 81%.

Example 8

Alkylation of Catechol with Oligomers of 1-Decene Using Benzenesulfonic Acid

A mixture of catechol (6.34 g, 0.058 mol), unhydrogenated oligomers of 1-decene (25 g, 0.058 mol; $C_{30}$, 95%; $C_{40}$, 5%; average $C_{30}$; containing 96% branched olefins); and benzenesulfonic acid (1.25 g) was heated with stirring at 140° C. for 6 hours. The homogeneous mixture was cooled to room temperature, dissolved in n-hexane (50 mL), and washed five times with 50 mL portions of water. The solvent was removed in a rotary evaporator by heating to 135° C. at 0.5 mm Hg to give 17 g of purple colored liquid product. The product had a hydroxyl number of 151 mg KOH/g, corresponding to a conversion of about 75%.

Example 9

Alkylation of Catechol With Oligomers of 1-Decene Using Trifluoromethanesulfonic Acid

A mixture of catechol (100 g, 0.175 mol), unhydrogenated oligomers of 1-decene (100 g, 0.175 mol; $C_{30}$, 11%; $C_{40}$, 62%; $C_{50}$, 27%; average $C_{42}$; containing 95% branched olefins), and trifluoromethanesulfonic acid (2.0 g) was heated with stirring at 140° C. for 6 hours. The homogeneous reaction mixture was cooled to room temperature, diluted with n-hexane (200 mL), and washed five times with 100 mL portions of aqueous isopropanol (water/isopropanol, 75/25, v/v). The solvent was removed in a rotary evaporator by heating to 110° C. at 0.5 mm Hg to give 110.9 grams of a dark amber liquid product. This product had a hydroxyl number of 105 mg KOH/g, corresponding to a conversion of about 64%.

Example 10

Alkylation of Catechol with 1-Dodecene Trimer Using p-Toluenesulfonic Acid

A mixture of catechol (43.8 g, 0.4 mol), unhydrogenated trimer of 1-dodecene (200 g, 0.4 mol; $C_{36}$; containing 92% branched olefins), and p-toluenesulfonic acid (10 g) was heated with stirring at 140° C. for 6 hours. The homogeneous reaction mixture was cooled to room temperature, diluted with n-hexane (200 mL), and washed five times with 100 mL portions of aqueous isopropanol (water/isopropanol, 75/25, v/v). The solvent was removed in a rotary evaporator by heating to 110° C. at 0.5 mm Hg to give 209.5 grams of a dark amber liquid product. This product had a hydroxyl number of 142 mg KOH/g, corresponding to a conversion of about 78%.

Example 11

Alkylation of Catechol with Dodecene Trimer Using Trifluoromethanesulfonic Acid

The procedure of Example 10 was repeated using trifluoromethanesulfonic acid (4.2 grams) as the catalyst instead of p-toluenesulfonic acid. After work-up as in Example 10, 229 grams of a liquid product was isolated. This product had a hydroxyl number of 149 mg KOH/g, corresponding to a conversion of about 81%.

The results of Examples 1–11 are summarized in Table I. Table I shows that the traditional insoluble sulfonic acid catalysts (Examples 1–4) do not catalyze the alkylation of catechol with alpha olefin oligomers. Soluble sulfonic acid catalysts (Examples 5–11), however, produce good to excellent yields of catechol alkylated with the alpha olefin oligomer.

Example 12 (Comparative)

Alkylation of Catechol with $C_{20}$–$C_{24}$ Alpha Olefins Using p-Toluenesulfonic Acid

A mixture of catechol (3800 g, 34.54 mol), $C_{20}$–$C_{24}$ normal alpha olefins (11,530 g, 38.67 mol; $C_{20}$, 49%; $C_{22}$, 42%; $C_{24}$, 9%; 85% alpha olefins), and p-toluenesulfonic acid (165 g) in 3300 mL of Chevron 350 Thinner was heated with stirring at 160° C. for 7 hours. The $C_{20}$–$C_{24}$ normal alpha olefin mixture is available from Chevron Chemical Company, San Ramon, Calif. Chevron 350 Thinner is a mixture of aromatics, paraffins and naphthenes and is available from Chevron Chemical Company. The solvent was removed by heating the mixture at 160° C. at reduced pressure (5 mm Hg) for 7 hours to give 15,000 grams of a dark amber oily product which solidified on standing at room temperature to a low melting wax. Analysis by GLC a monoalkyl to dialkyl weight ratio of 46/54. The product had a hydroxyl number of 149 mg KOH/g.

Example 12 shows that catechol alkylated with a $C_{20}$–$C_{24}$ alpha olefin mixture is a solid at room temperature. By comparison, catechol alkylated with alpha olefin oligomers (Examples 5–11) gives a liquid alkyl catechol product.

TABLE I

Alkylation of Catechol with Alpha Olefin Oligomers

| Example No. | AOO[1] | Catalyst | Catalyst Type[2] | Rxn. Time (Hours) | Rxn. Temp. (°C.) | Percent Conv.[3] |
|---|---|---|---|---|---|---|
| 1 | A | Amberlyst-15 ® | Insoluble | 10 | 135 | NR[4] |
| 2 | A | Amberlyst-36 ® | Insoluble | 20 | 140 | NR |
| 3 | A | XU-40036 | Insoluble | 20 | 140 | NR |
| 4 | A | Nafion-H ® | Insoluble | 20 | 140 | NR |
| 5 | A | Methanesulfonic Acid | Soluble | 7 | 140 | 69, 64 |
| 6 | A | p-Toluenesulfonic Acid | Soluble | 7 | 140 | 61, 55 |
| 7 | A | Trifluoromethanesulfonic Acid | Soluble | 4 | 135 | 81 |
| 8 | B | Benzenesulfonic Acid | Soluble | 6 | 140 | 75 |
| 9 | C | Trifluoromethanesulfonic Acid | Soluble | 6 | 140 | 64 |
| 10 | D | p-Toluenesulfonic Acid | Soluble | 6 | 140 | 78 |
| 11 | D | Trifluoromethanesulfonic Acid | Soluble | 6 | 140 | 81 |

[1]Alpha olefin oligomer (AOO) composition:
A = $C_{30}$, 62%; $C_{40}$, 28%; $C_{50}$, 10%; average $C_{35}$; (containing 90% branched olefins)
B = $C_{30}$, 95%; $C_{40}$, 5%; average $C_{30}$; (containing 96% branched olefins)
C = $C_{30}$, 11%; $C_{40}$, 62%; $C_{50}$, 27%; average $C_{42}$; (containing 95% branched olefins)
D = $C_{36}$; (containing 92% branched olefins)
[2]Indicates if catalyst was soluble or insoluble under the alkylation reaction conditions.
[3]Percent conversion (alkylation) measured by hydroxyl number and/or SFC analysis.
[4]No reaction, i.e no alkylated product detected.

What is claimed is:

1. A process for the alkylation of an aromatic polyol, having from 1 to 3 aromatic rings and from 2 to 4 hydroxyl groups and wherein at least two of said hydroxyl groups are directly connected to adjacent aromatic ring carbon atoms, with an alpha olefin oligomer of an alpha olefin having from 8 to 14 carbon atoms and wherein said oligomer has from 24 to 60 carbon atoms and greater than 85 percent branched olefins to produce a liquid alkyl aromatic polyol product, which comprises reacting said aromatic polyol with said alpha olefin oligomer under alkylation reaction conditions in the contact presence of a catalytic amount of an organic sulfonic acid catalyst which is soluble under reaction conditions and thereafter recovering a liquid alkyl aromatic polyol product.

2. A process according to claim 1 wherein the aromatic polyol has the formula:

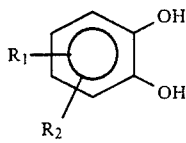

wherein $R_1$ and $R_2$ can be the same or different and are selected from the group consisting of hydrogen, hydroxy, lower alkyl of 1 to 8 carbon atoms, and lower alkoxy of 1 to 8 carbon atoms.

3. A process in accordance with claim 2 wherein said alpha olefin has from 10 to 12 carbon atoms and wherein the molar ratio of said aromatic polyol to said alpha olefin oligomer is from about 10:1 to 0.5:1.

4. A process in accordance with claim 2, wherein the reaction temperature is from 50° C. to 200° C. and wherein the reaction mixture is essentially homogeneous.

5. A process in accordance with claim 4 wherein said aromatic polyol is catechol.

6. A process in accordance with claim 4 wherein the catalyst is an aromatic sulfonic acid.

7. A process according to claim 6 wherein the catalyst is p-toluenesulfonic acid.

8. A process according to claim 6 wherein the catalyst is benzenesulfonic acid.

9. A process according to claim 8 wherein said aromatic polyol is catechol.

10. A process according to claim 4 wherein the catalyst is trifluoromethanesulfonic acid.

11. A process according to claim 4 wherein the catalyst is methanesulfonic acid.

12. A process according to claim 2 wherein said alpha olefin oligomer is a trimer, tetramer, pentamer, or mixture thereof.

13. A process according to claim 12 wherein said alpha olefin is selected from the group consisting of 1-decene and 1-dodecene.

14. A process according to claim 13 wherein said aromatic polyol is catechol.

15. A process according to claim 14 wherein said catalyst is p-toluenesulfonic acid.

16. A process according to claim 2 wherein said alpha olefin oligomers contain greater than 90 weight percent branched olefins.

17. A process according to claim 16 wherein said alpha olefin is selected from the group consisting of 1-decene and 1-dodecene.

18. A process according to claim 17 wherein said alpha olefin is 1-decene; said aromatic polyol is catechol and said catalyst is p-toluenesulfonic acid.

19. A process according to claim 6 wherein said liquid product is heated under desulfonation conditions to desulfonate said aromatic sulfonic acid; and thereafter recovering a liquid alkyl aromatic polyol product substantially free of said aromatic sulfonic acid catalyst.

20. A process according to claim 17 wherein said oligomer has from 30 to 50 carbon atoms.

21. A process according to claim 6 wherein said oligomer has from 30 to 50 carbon atoms.

22. A process according to claim 18 wherein said oligomer has from 30 to 50 carbon atoms.

* * * * *